(12) United States Patent
Fremy et al.

(10) Patent No.: US 12,227,468 B2
(45) Date of Patent: *Feb. 18, 2025

(54) PROCESS FOR THE CO-PRODUCTION OF METHYL MERCAPTAN AND OF DIMETHYL DISULFIDE FROM CARBON OXIDES

(71) Applicant: Arkema France, Colombes (FR)

(72) Inventors: Georges Fremy, Lacq (FR); Jean-Michel Raymond, Cauneille (FR); Eric Lamant, Lacq (FR); Helori Salembier, Lacq (FR)

(73) Assignee: Arkema France, Colombes (FR)

( * ) Notice: Subject to any disclaimer, the term of this patent is extended or adjusted under 35 U.S.C. 154(b) by 338 days.

This patent is subject to a terminal disclaimer.

(21) Appl. No.: 17/740,839

(22) Filed: May 10, 2022

(65) Prior Publication Data
US 2022/0363630 A1    Nov. 17, 2022

(30) Foreign Application Priority Data
May 11, 2021   (FR) ...................................... 2104979

(51) Int. Cl.
C07C 319/02    (2006.01)
C07C 319/06    (2006.01)
(Continued)

(52) U.S. Cl.
CPC .......... C07C 319/02 (2013.01); C07C 319/06 (2013.01); C07C 319/16 (2013.01); C07C 319/24 (2013.01); C07C 319/28 (2013.01)

(58) Field of Classification Search
CPC ........................... C07C 319/02; C07C 319/24
See application file for complete search history.

(56) References Cited

U.S. PATENT DOCUMENTS

| 4,665,242 A | 5/1987 | Boulinguiez et al. |
| 6,743,951 B2 | 6/2004 | Fremy |

(Continued)

FOREIGN PATENT DOCUMENTS

| EP | 0171092 A2 | 2/1986 |
| EP | 0171312 A1 | 2/1986 |

(Continued)

OTHER PUBLICATIONS

French Search Report and Written Opinion for French Application No. 2104977, dated Dec. 2, 2021, 7 pages.

Primary Examiner — Rosalynd A Keys
(74) Attorney, Agent, or Firm — Buchanan Ingersoll & Rooney PC

(57) ABSTRACT

The invention relates to a process for the co-production of methyl mercaptan and of dimethyl disulfide, comprising the following successive steps:
a) reaction of at least one carbon oxide in the presence of hydrogen sulfide ($H_2S$) and hydrogen to form a stream (M) comprising methyl mercaptan, water, and possibly unreacted hydrogen sulfide,
b) purification of the stream (M) to obtain a stream (N) enriched in methyl mercaptan and a stream containing the uncondensable compounds ($M_{uncond}$),
c) optional recycling of the stream of uncondensable compounds ($M_{uncond}$) obtained from step b) into step a),
d) recovery of a first portion of the stream (N) including methyl mercaptan purified in step b),
e) oxidation with sulfur of the second portion of the stream (N) of methyl mercaptan, to form a stream (O) comprising dimethyl disulfide, hydrogen sulfide, and possibly unreacted methyl mercaptan,
f) purification of the stream (O) to separate, on the one hand, the enriched dimethyl disulfide and, on the other
(Continued)

hand, the hydrogen sulfide and possibly the methyl mercaptan that has not reacted in step e), g) recycling of the hydrogen sulfide and possibly of the methyl mercaptan isolated in step f) into the stream (M) obtained from step a), h) recovery of the dimethyl disulfide isolated in step f).

11 Claims, 1 Drawing Sheet

(51) Int. Cl.
*C07C 319/16* (2006.01)
*C07C 319/24* (2006.01)
*C07C 319/28* (2006.01)

(56) References Cited

U.S. PATENT DOCUMENTS

| | | |
|---|---|---|
| 8,791,292 B2 | 7/2014 | Forquy et al. |
| 9,944,594 B2 * | 4/2018 | Fremy ............... B01J 23/745 |
| 10,377,704 B2 | 8/2019 | Fremy et al. |
| 10,550,077 B2 | 2/2020 | Fremy et al. |
| 11,104,642 B2 | 8/2021 | Fremy et al. |
| 11,897,837 B2 * | 2/2024 | Fremy ................ C07C 319/28 |
| 2008/0262270 A1 | 10/2008 | Barth et al. |
| 2010/0094059 A1 | 4/2010 | Yang et al. |
| 2010/0286448 A1 | 11/2010 | Yang et al. |
| 2020/0331852 A1 | 10/2020 | Fremy et al. |

FOREIGN PATENT DOCUMENTS

| | | |
|---|---|---|
| EP | 0976726 A1 | 2/2000 |
| FR | 2935142 A1 | 2/2010 |
| WO | 2005040082 A2 | 5/2005 |
| WO | 2014154885 A1 | 10/2014 |
| WO | 2016001553 A1 | 1/2016 |
| WO | 2016001554 A1 | 1/2016 |
| WO | 2019122072 A1 | 6/2019 |

* cited by examiner

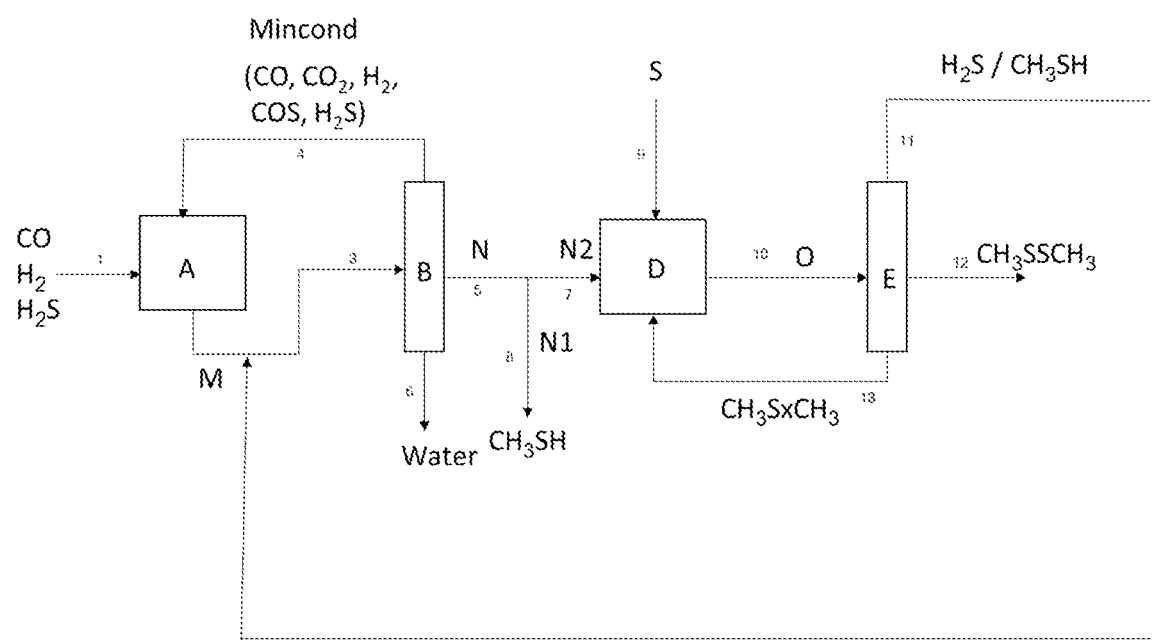

PROCESS FOR THE CO-PRODUCTION OF METHYL MERCAPTAN AND OF DIMETHYL DISULFIDE FROM CARBON OXIDES

CROSS-REFERENCE TO RELATED APPLICATIONS

This application claims priority to French Application No. 2104979, filed May 11, 2021, the disclosure of the application being incorporated herein by reference in its entirety for all purposes.

FIELD OF THE INVENTION

The present invention relates to a process for the co-production of methyl mercaptan and of dimethyl disulfide from carbon oxides.

Mercaptans are of great interest industrially and are currently in widespread use in the chemical industries, notably as starting materials in the synthesis of more complex organic molecules. For example, methyl mercaptan (noted as $CH_3SH$ or MeSH hereinbelow) is used as a starting material in the synthesis of methionine, an essential amino acid for animal nutrition. Methyl mercaptan is also used in the synthesis of dimethyl disulfide (noted as DMDS hereinbelow).

Dimethyl disulfide is of great industrial interest and is very widely used industrially. For example, and in a non-limiting manner, it is used as a catalyst sulfurization additive, notably in the hydrotreatment of petroleum cuts, as an anti-coking and anti-CO additive in petroleum feedstocks subjected to steam cracking for the production of ethylene, or as a soil fumigation agent in agriculture.

In comparison with other products used in these applications, for instance di-tert-alkyl polysulfides, DMDS has many advantages. For example, DMDS has a high sulfur content (68%) and non-coking degradation products ($CH_4$, $H_2S$). Furthermore, in these applications, DMDS leads to performance qualities that are generally higher than those of the other commercial products usually used, for example di-tert-alkyl polysulfides.

At the present time, it is known how to produce methyl mercaptan via various synthetic routes.

Methyl mercaptan may be produced from methanol ($CH_3OH$) and hydrogen sulfide ($H_2S$) according to reaction (1) below:

$$CH_3OH + H_2S \rightarrow CH_3SH + H_2O \qquad (1)$$

It is also possible to prepare methyl mercaptan from carbon monoxide (CO) according to reaction (2) below:

$$CO + 2H_2 + H_2S \rightarrow CH_3SH + H_2O \qquad (2)$$

Other processes are described in the literature and combine various reactions such as:

formation of $CS_2$ and $H_2$ from methane, $H_2S$ and sulfur, according to reaction (3):

$$CH_4 + S + H_2S \rightarrow CS_2 + 3 H_2 \qquad (3)$$

hydrogenation of $CS_2$, with the hydrogen formed above, according to reaction (4):

$$CS_2 + 3 H_2 \rightarrow CH_3SH + H_2S \qquad (4)$$

The step for the synthesis of dimethyl disulfide is conventionally performed by oxidation with sulfur according to reaction (5) below:

$$2 CH_3SH + S \rightarrow CH_3SSCH_3 + H_2S \qquad (5)$$

This oxidation of methyl mercaptan with sulfur, catalysed with homogeneous or heterogeneous, organic or mineral basic agents, in batch mode or continuous mode, is accompanied by a formation of hydrogen sulfide and also of dimethyl polysulfides, noted as MeSxMe with a sulfur rank x of greater than 2. Moreover, this synthetic step generally requires a large excess of methyl mercaptan.

Now, in the context of the current ecological considerations, there is at the present time a real need for a process for the synthesis of methyl mercaptan and of dimethyl disulfide that is more environmentally friendly, while at the same time maintaining high yields.

BRIEF DESCRIPTION OF THE INVENTION

Thus, one object of the present invention is a process for the co-production of methyl mercaptan and of dimethyl disulfide, comprising the following successive steps:

a) reaction of at least one carbon oxide in the presence of hydrogen sulfide ($H_2S$) and hydrogen to form a stream (M) comprising methyl mercaptan, water, and possibly unreacted hydrogen sulfide, b) purification of the stream (M) to obtain a stream (N) enriched in methyl mercaptan and a stream containing the uncondensable compounds ($M_{uncond}$), c) optional recycling of the stream of uncondensable compounds ($M_{uncond}$) obtained from step b) into step a), d) recovery of a first portion of the stream (N) including methyl mercaptan purified in step b), e) oxidation with sulfur of the second portion of the stream (N) of methyl mercaptan, to form a stream (O) comprising dimethyl disulfide, hydrogen sulfide, and possibly unreacted methyl mercaptan, f) purification of the stream (O) to separate, on the one hand, the enriched dimethyl disulfide and, on the other hand, the hydrogen sulfide and possibly the methyl mercaptan that has not reacted in step e), g) recycling of the hydrogen sulfide and possibly of the methyl mercaptan isolated in step f) into the stream (M) obtained from step a), h) recovery of the dimethyl disulfide isolated in step f).

This process allows the continuous synthesis of methyl mercaptan and of dimethyl disulfide. This co-production of products makes it possible to reduce the energy cost of the synthesis. This energy saving is a first ecological advantage.

It also enables the production of each product to be modulated according to the demand. For example, the synthesis of methyl mercaptan may be favoured over that of dimethyl disulfide. This flexibility in the process is also an advantage. It is also possible, depending on the need, to produce only methyl mercaptan, i.e. to stop the process at step d). Similarly, if need be, all of the stream (N) may be engaged in the oxidation step e). This flexibility of the process is a considerable advantage. It enables the production of the products to be adapted according to the needs, in one and the same facility.

Next, this co-production enables the impurities of the final product to be recycled. The methyl mercaptan which has not reacted during the oxidation reaction with sulfur and the hydrogen sulfide generated during this oxidation step are recycled into the methyl mercaptan synthesis. These impurities are usually incinerated, leading to the formation of sulfur oxides ($SO_2$), which are potentially responsible for acid rain. At the present time, these discharges are no longer tolerated. Now, the recycling of all of these light impurities avoids their incineration. The recycling step g) according to the invention thus allows recycling of the hydrogen sulfide on a closed facility. As hydrogen sulfide is a toxic gas, closed recycling makes it possible to limit the handling of this gas, and thereby to limit the accidents.

It would also be possible to separate the hydrogen sulfide from the methyl mercaptan to economically exploit these impurities. However, this separation is very difficult, requiring distillation apparatus equipped with a very tall column. As a result, this separation is highly energy-intensive. Thus, the recycling of these two impurities into the same stream (i.e. not separated) to be incorporated into an already-existing purification step of the synthetic process is a solution that is simple and very advantageous in energy terms; what is more, the oxidation step with sulfur generally requires a very large excess of methyl mercaptan.

This recycling is incorporated into a purification step that is essential to the synthetic process. This recycling is thus simple to perform and inexpensive in energy terms. It does not require an additional step in the synthetic process.

Finally, these impurities, which are compounds from the first synthetic step: reagent for the hydrogen sulfide and product for the methyl mercaptan, enrich this first step of the process, leading to a reduction in the consumption of starting materials.

As regards the reaction, the claimed process covers the following two reactions:

regarding carbon monoxide: $CO+2H_2+H_2S \rightarrow CH_3SH+H_2O$ regarding carbon dioxide: $CO_2+3H_2+H_2S \rightarrow CH_3SH+2H_2O$ and then

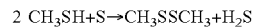

These reactions may be simplified the following manner, when the hydrogen sulfide is recycled into the first step:

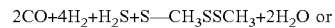

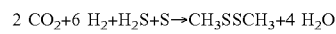

BRIEF DESCRIPTION OF THE FIGURE

FIG. 1 is a scheme of the device performing the claimed process.

DETAILED DESCRIPTION OF THE INVENTION

Other characteristics, aspects, objects and advantages of the present invention will emerge even more clearly on reading the description that follows.

It is pointed out that the expressions "from . . . to . . . " and "between . . . and . . . " used in the present description should be understood as including each of the limits mentioned.

The process according to the invention comprises the eight abovementioned consecutive steps: steps a) to h). This process may include intermediate purification steps.

Step a)—Reaction:

In step a), at least one carbon oxide, hydrogen and hydrogen sulfide are reacted, preferably in gaseous form, optionally in the presence of at least one catalyst so as to form a stream (M), preferably in gaseous form, comprising methyl mercaptan, water and possibly unreacted hydrogen sulfide. Depending on the degree of conversion of the reaction, the stream (M) may include hydrogen, unreacted hydrogen sulfide, carbonyl sulfide (COS) and possibly said at least one unreacted carbon oxide.

This synthetic step requires hydrogen sulfide. It is possible for this hydrogen sulfide to be engaged in the reaction as such, as mentioned in the above paragraph, or as illustrated in the above reaction schemes. It is also possible to generate the hydrogen sulfide in situ from sulfur and hydrogen. According to this variant, the reagents of the reaction are the carbon oxide(s), sulfur and hydrogen.

The carbon oxide may be carbon monoxide, carbon dioxide or a mixture thereof.

In particular, step a) is performed at a temperature of between 200° C. and 500° C., preferably between 200° C. and 400° C. In particular, step a) is performed at a pressure between 1 and 100 bar absolute, preferably between 3 and 30 bar absolute.

Preferably, in step a), the carbon oxide/S/$H_2S$/$H_2$ mole ratio is between 1/0/0.05/0.05 and 1/20/40/100. Preferably, it is between 1/0/0.5/1 and 1/0/10/20. In particular, it is 1/0/1/2.

Preferably, in step a), in the absence of sulfur, the $CO/H_2$/$H_2S$ ratio is between 1/0.05/0.05 and 1/40/100. Preferably, it is between 1/0.5/1 and 1/10/20. In particular, it is 1/2/1.

Step a) may be performed on one or more catalytic beds, which are preferably fixed. It may be performed in a reactor comprising one or more reaction zones, the reagent(s) possibly being fed between the various zones. Thus, the reagents, preferably $H_2$ and/or $H_2S$, may be introduced separately onto the various catalytic beds or reaction zones.

Said at least one catalyst used in step a) is known and may notably be chosen from:

catalysts based on molybdenum and potassium supported on zirconia such as $K_2MoO_4/ZrO_2$, as described in WO 2019/122072. These catalysts are tested at a temperature of 320° C. and at a pressure of 10 bar using a $CO/H_2/H_2S$ ratio of 1/2/1.

catalysts based on molybdenum and potassium of Mo—S—K and/or Mo—O—K type on a hydroxyapatite support such as $K_2MoS_4/Ca_{10}(PO_4)_6(OH)_2$ or $K_2MoO_4/Ca_{10}(PO_4)_6(OH)_2$ as described in WO 2014/154885. These catalysts are tested at a temperature of 280° C. and at a pressure of 10 bar using a $CO/H_2/H_2S$ ratio of 1/2/1.

the catalysts described in patent application US 2010/0286448, composed of a porous support such as $SiO_2$, $TiO_2$, silica-aluminas, zeolites and carbon nanotubes, onto which a metal has been electrolytically deposited. $K_2MoO_4$, and also another metal oxide acting as promoter, are then impregnated onto this support.

catalysts based on Mo and K (in particular $K_2MoO_4$) promoted with $TeO_2$ and supported, such as $K_2MoO_4/TeO_2/SiO_2$, described in US 2010/094059. The catalyst $K_2MoO_4/TeO_2/SiO_2$ is tested for a temperature of 300° C. and at a pressure of 2 bar, taking a $CO/H_2/H_2S$ ratio of 1/1/2 and an hourly space velocity of 2000 $h^{-1}$.

International patent application WO 2005/040082 describes several catalysts and notably a catalyst comprising an active component based on Mo—O—K, an active promoter and optionally a support. The catalysts illustrated are $K_2MoO_4/Fe_2O_3/NiO$ or $K_2MoO_4/CoO/CeO_2/SiO_2$, each supported on silica. These catalysts are tested at a temperature of 320° C. and at a pressure of 7 bar, taking a $CO/H_2/H_2S$ ratio of 1/1/2 and an hourly space velocity of 3000 $h^{-1}$.

Step b)—Purification:

At least one step of purification of said stream (M) is performed to obtain a stream (N) enriched in methyl mercaptan and a stream ($M_{uncond}$) containing the uncondensable compounds. Preferably, said purification step allows the $H_2S$ to be separated out from the stream (M).

The purification step b) may comprise one or more condensation steps, optionally followed by one or more decantation steps, optionally followed by one or more distillation steps. Preferably, said purification step b) comprises at least one condensation step (notably as described below) and optionally a distillation step (notably as described below).

Condensation

Preferably, the stream (M) is condensed.

Any type of condenser may be used for this operation, such as tubular or plate exchangers. Preferably, the condenser has separated fluids, i.e. there is no contact between the gases to be condensed and the refrigerant fluid. The refrigerant fluid may be liquid or gaseous such as air, water, glycols, brine, ammonia, freons or oils.

The condensation temperature may be between 20° C. and 70° C., preferably between 30° C. and 60° C. The pressure may be between 1 bar absolute and 100 bar absolute. The object is to condense a maximum amount of methyl mercaptan and water relative to the uncondensable compounds, which will allow easy separation of the liquid and gas phases.

The term "uncondensable compounds" notably means the compounds which remain in gaseous form at the temperatures and pressures of said production process, notably after the condensation step. Uncondensable compounds that may notably be mentioned include the unreacted carbon oxide(s), i.e. carbon monoxide and/or carbon dioxide, hydrogen, the unreacted hydrogen sulfide, possibly carbonyl sulfide (COS), and any other uncondensable inert compound produced or introduced during said process. Preferably, the term "uncondensable compounds" means the unreacted carbon oxide(s), the unreacted hydrogen, the unreacted hydrogen sulfide, and possibly the carbonyl sulfide (COS).

These uncondensable compounds are separated, to constitute a stream $M_{uncond}$. The condensed stream ($M_{Cond}$) may then undergo the following purification step(s).

Separation of the Water

The water separation step may be performed via any conventional technique and in particular by decantation. Preferably, the stream ($M_{Cond}$) is in liquid form. Thus, the following are separated, preferably by decantation, from the stream ($M_{Cond}$):
 an organic phase ($M_{org}$) comprising methyl mercaptan and possibly residual water; and
 an aqueous phase ($M_{aq}$).

In particular, in the water separation step, the aqueous phase ($M_{aq}$) comprises at least 50% by weight, preferably at least 70%, more preferentially at least 90% by weight of water, relative to the total weight of the water present in the stream (M).

Distillation of the $H_2S$

The organic phase ($M_{org}$) comprising methyl mercaptan may also undergo a distillation step so as to remove the traces of hydrogen sulfide that may still be present in this stream.

During the distillation, the pressure may be between 0.05 and 40 bar absolute, preferably between 1 and 25 bar absolute and/or the temperature may be between −60° C. and +60° C., preferably between 10 and 50° C., at the top of the column; and between +20° C. and +200° C., preferably between 20° C. and 100° C., at the bottom of the column.

Depending on the purification steps of step b); the stream (N) may be the stream ($M_{cond}$), the stream ($M_{org}$) or the stream of methyl mercaptan obtained from the above mentioned distillation step.

Additional Step of Drying of the Stream (N)

The stream (N) may be dried over molecular sieves, over $MgSO_4$, with $H_2SO_4$, over $CaCl_2$ or by azeotropic distillation.

The stream recovered on conclusion of step b) is noted (N).

According to a preferred embodiment, the purification step b) comprises one or more condensation steps, followed by one or more decantation steps, and optionally one or more distillation steps.

According to a preferred embodiment, the purification step b) comprises a condensation step, followed by a decantation step, and optionally a distillation step.

Step c)—Optional Recycling

The stream $M_{uncond}$ in gaseous form, recovered during the purification step b) and which may comprise the unreacted carbon monoxide and/or carbon dioxide, the unreacted hydrogen sulfide, any unreacted hydrogen and the carbonyl sulfide that may be present, may be recycled, before step a), so as to once again undergo this reaction. A purge may be provided, so as to regulate the amount of the stream to be recycled.

Step d)—Recovery of the Methyl Mercaptan:

The process according to the invention then comprises a step of recovery of the methyl mercaptan. A portion of the stream (N), noted (N1), is recovered for optional engagement in another process. The second portion of the stream (N), noted (N2), is, itself, engaged in the next step of the process according to the invention: step e).

Step e)—Oxidation:

In step e), a portion of the methyl mercaptan (N2) obtained on conclusion of step d) is reacted, by oxidation with sulfur to form a stream (O) comprising dimethyl disulfide, hydrogen sulfide, possibly unreacted methyl mercaptan, and possibly dimethyl polysulfides.

This step is described, for example, in patent application EP 0 976 726. For example, step e) may be performed at elevated temperature and under pressure, for example between 20° C. and 200° C., preferably between 20° C. and 100° C., and the pressure is between 2 and 30 bar absolute, preferably between 2 and 15 bar absolute, typically, for example, at about 70° C., under about 6 bar in the case of oxidation with sulfur of methyl mercaptan.

The oxidation reaction e) is performed in a reactor, which may contain a catalyst. A basic catalyst is preferably used. This basic catalyst may be homogeneous, two-phase or heterogeneous (solid). When the catalyst is homogeneous, i.e. soluble in the mercaptan, amines, amidines and guanidines are preferred. When the basic catalyst forms a two-phase aqueous phase, all water-soluble bases, such as sodium hydroxide, potassium hydroxide, and alkali metal, alkaline-earth metal or ammonium hydroxides are preferred. When the base envisaged is a solid, any solid having a basic nature may be envisaged, such as MgO, CaO, alumina or any other support (silica, zirconias, titanium oxides, hydrotalcites, hydroxyapatites, etc.) optionally doped with alkali metal or alkaline-earth metal oxides, or optionally doped zeolites. Preferably, the heterogeneous catalysts are basic ion-exchange resins; more preferably, the heterogeneous catalyst is the Amberlyst® A21 resin sold by the company DuPont.

The methyl mercaptan/sulfur mole ratio of the oxidation step e) may be between 0.1 and 100, preferably between 1 and 50, and more preferentially between 1 and 20.

This oxidation step may make it possible to form a gas stream (O12) comprising hydrogen sulfide and possibly unreacted methyl mercaptan and a liquid stream (O11) comprising the dimethyl disulfide, and residual dimethyl polysulfides.

Additional Degassing Step:

The stream (O) or the liquid stream (O11) may then be treated in a degasser so as to remove from the liquid stream the residual gases, such as the hydrogen sulfide or the methyl mercaptan that may be present, forming the stream (O22). The degassed liquid stream is named (O21).

Additional Step of Retrogradation of the Polysulfides

The liquid stream (O21) obtained from the preceding additional degassing step or the stream (O11) obtained from the oxidation step may undergo a step of retrogradation of the polysulfides with a high sulfur rank to polysulfides with a lower sulfur rank, and ideally to disulfides, so as to convert the residual polysulfides into dimethyl disulfide. The reactor used for this retrogradation step is known as a finisher. It includes an inlet for methyl mercaptan introduced in excess so as to increase the reaction conversion. This finishing step may make it possible to form a gas stream (O32) comprising hydrogen sulfide and possibly unreacted methyl mercaptan and a liquid stream (O31) comprising the dimethyl disulfide.

Additional Degassing Step:

The liquid stream (O31) may undergo an additional degassing step. The liquid stream (O31) may be treated in a degasser so as to remove the residual gases, such as the hydrogen sulfide and possibly the unreacted methyl mercaptan, forming the stream (O42). The degassed liquid stream is named (O41).

Step f)—Purification

The process according to the invention includes at least one step of purification of the liquid stream obtained from the oxidation step e). This liquid stream may be the stream (O) obtained directly from the oxidation reaction e) or the streams (O11), (O21), (O31) or (O41) depending on the presence of additional degassing or retrogradation steps. This step makes it possible to separate, on the one hand, the enriched dimethyl disulfide and, on the other hand, the hydrogen sulfide and possibly the methyl mercaptan that has not reacted in step e). Such a step may notably make it possible to separate:
the enriched dimethyl disulfide,
the hydrogen sulfide possibly with the unreacted methyl mercaptan, and
impurities such as the heavy products, the volatile compounds, the hydromethyl disulfide or the mercaptomethyl methyl sulfide.

This purification step f) may include a succession of distillation steps for isolating the dimethyl disulfide. In particular, said purification step f) may include one or more distillation steps, and optionally one or more basic catalysis steps.

According to a first embodiment, the purification step f) may be performed via any conventional technique and in particular in steps f1) to f4) as described below. In particular, said purification step corresponds to step f1) or f6) as described below.

Step f1)—Removal of the H$_2$S formed:

The purification step f1), preferably by distillation, produces:
a gas stream (P12) comprising hydrogen sulfide and possibly unreacted methyl mercaptan; and
a liquid stream (P11) predominantly comprising dimethyl disulfide.

In the distillation, the pressure may be between 0.05 and 15 bar absolute, preferably between 1 and 10 bar absolute. The temperature at the bottom of the column may be between 50 and 300° C., preferably between 50 and 200° C. At the top of the column, the temperature may be between 30 and 200° C., preferably between 30 and 120° C.

Step f2)—Removal of the heavy products:

A second distillation of the stream (P11) may then be performed so as to obtain:
a stream (P22) constituting the column head and predominantly comprising dimethyl disulfide and residual traces of volatile impurities; and
a stream (P21) constituting the column tail and comprising a mixture of heavy impurities.

The stream of the heavy distillation impurities (P21) may be recycled into the dimethyl disulfide synthesis step, notably into step e) or f1), as defined above. It is possible to equip the recycling pipe with a purge so as to avoid the accumulation of impurities in the process.

Step f3)—Removal of the hydromethyl disulfide by basic reaction:

The stream obtained from step e) or the stream (P11) and/or the stream (P22) may be reacted in a reactor including a basic catalyst so as to convert the hydromethyl disulfide into dimethyl trisulfide according to the following reaction:

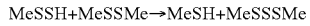

MeSSH+MeSSMe→MeSH+MeSSSMe

The basic catalyst may be of any type known to a person skilled in the art. Said basic catalyst is preferably heterogeneous relative to the reaction medium, so as to facilitate its subsequent separation. Thus, the basic catalyst may be chosen, for example, from anion-exchange resins, such as Amberlyst® A21 from DuPont, basic catalysts in free amine form, aluminas doped with sodium oxide and/or with potassium oxide, magnesium oxide (MgO) and basic zeolites. It is also possible to use the catalysts listed above for the oxidation reaction e). Preferably, the basic catalyst is an anion-exchange resin.

Step f4—Removal of the traces of volatile compounds:

A third distillation of the stream obtained from step f3) may finally be performed so as to obtain:
a stream (P31) at the top of the column, comprising the traces of methyl mercaptan formed in step f3), and
a stream (P32) constituting the column tail and comprising dimethyl disulfide.

According to a second embodiment, the purification step f) may be performed in steps f5) and f6) as described below.

Step f5—Removal of the undesirable impurities by basic reaction:

The liquid stream (O) obtained directly from the oxidation reaction e), or the streams (O11), (O21), (O31) or (O41) depending on the presence of additional degassing or retrogradation steps, may undergo a basic catalysis reaction. Thus, these streams may enter a reactor including a basic catalyst so as to remove the undesirable impurities.

The catalyst used may be the one disclosed for step f3) defined above.

Step f6—Removal of the traces of volatile compounds and of heavy impurities:

A distillation of the stream obtained from step f5) may then be performed so as to obtain:
a stream at the top of the column comprising hydrogen sulfide and traces of methyl mercaptan,
a stream removed in the side position, including dimethyl disulfide, and a stream constituting the column tail and comprising the mixture of heavy impurities.

The distillation column used for performing this step may be a column with side withdrawal or a partition column.

If a partition column is used, then the conditions of the column may be the following. The column head temperature may be between 0° C. and 150° C., preferably between 10° C. and 100° C. The column middle temperature may be between 30° C. and 200° C., preferably between 50° C. and 150° C. The column tail temperature may be between 50° C. and 250° C., preferably between 80° C. and 180° C. The pressure inside the column may be between 0.05 bar and 30 bar absolute, preferably between 0.1 and 5 bar absolute. The reflux ratio, defined as being the mass ratio between the liquid reinjected into the top of the column to the distillate containing the light impurities at the top of the column, is between 0 (no reflux) and 100, preferably between 0 and 10.

According to a third embodiment, it is possible to incorporate a distillation column prior to steps f5) and f6), so as to remove the volatile impurities before the basic catalysis step.

Recycling Step g)

The recycling step g) leads the stream to be recycled before the purification step b), which in particular removes the hydrogen sulfide from the stream (M) to be purified, preferably by condensation, optionally followed by decantation and/or distillation.

The hydrogen sulfide and possibly the methyl mercaptan recovered during these steps e) and/or f), and optionally the additional steps, is recycled into the stream (M) obtained from step a), i.e. it is injected into the stream (M) so as to undergo the purification step b). For example, it may be injected before the condensation step or before the separation step or before the distillation step, preferably before the condensation step. Thus, the streams (O12), (O22), (O32), (O42), (P12) and (P31) may be pooled as a single stream and reinjected into the stream (M).

A portion or all of the stream may be reinjected into the stream (M). When a portion of the stream is reinjected, the recycling pipe contains a purge, so as to regulate the proportions of the recycled stream. Preferably, all of the stream of hydrogen sulfide, and possibly the methyl mercaptan recovered in steps e) and/or f), is recycled into the stream (M) obtained from step a).

Recovery Step h)

The dimethyl disulfide is finally recovered.

FIG. 1 shows one embodiment of steps a) to h) of the process according to the invention.

The reaction step a) is performed in a reactor A using at least one carbon oxide, hydrogen sulfide and hydrogen.

The stream of carbon oxide(s), of hydrogen sulfide and of hydrogen enters via pipe 1 into the reactor A. The stream M leaving the reactor A via pipe 3 comprises methyl mercaptan, water, unreacted hydrogen sulfide, unconverted carbon oxide(s), unconverted hydrogen and possibly sulfur-based by-products.

The purification step b) is performed in a device B, such as a separator. The stream of uncondensable compounds $M_{uncond}$, such as the unreacted carbon oxide(s), i.e. carbon monoxide and/or carbon dioxide, hydrogen, the unreacted hydrogen sulfide, possibly carbonyl sulfide (COS), and any other uncondensable inert compound produced or introduced during said process, is separated out and removed via a pipe 4, the aqueous stream $M_{aq}$ is removed via a pipe 6 and the stream N comprising methyl mercaptan and possibly sulfur-based by-products leaves the device B via pipe 5.

Pipe 4 is connected to the reactor A. Pipe 4 may include a purge.

Pipe 5 is divided into a pipe 7 and a pipe 8. Pipe 8 allows recovery of the methyl mercaptan (step d) of the process) and pipe 7 conveys the rest of the stream N to the reactor D.

The oxidation step e) is performed in a reactor D. The sulfur is introduced into the reactor D via pipe 9. The stream O leaving the reactor D via pipe 10 comprises dimethyl disulfide, hydrogen sulfide, unreacted methyl mercaptan and possibly sulfur-based by-products.

The purification step f) is performed in a device E, such as a distillation column. The stream of hydrogen sulfide and of unreacted methyl mercaptan is removed at the top of the column via a pipe 11, and the column tail is recycled via a pipe 13 into the reactor D. Pipes 11 and 13 may include a purge. The column middle including the dimethyl disulfide is recovered via a pipe 12.

Pipe 11 recycles the column head comprising the hydrogen sulfide and the unreacted methyl mercaptan into pipe 3 bringing the stream M to the purification device B.

The examples that follow illustrate the present invention but are not in any way limiting.

EXAMPLES

Removal of the Sulfur-Based Waste

Two units for the production of DMDS and MeSH were compared. One does not include step g) of recycling the streams after step a). The other is a unit according to the invention and includes this recycling step g). 50000 T/year of MeSH and 50000 T/year of DMDS are produced, i.e. for each of the two products, a production of 151.5 T/day (on a basis of 330 days/year), or 6.3 T/h (on a basis of 24 h/day). Under these conditions, the stream 11 of FIG. 1 contains 2.2 T/h of $H_2S$ and 2.3 T/h of MeSH.

TABLE 1

| | Emission of $SO_2$ (T/h) | Loss of MeSH yield on the two units combined (%) |
|---|---|---|
| Unit for production of 50 000 tonnes/year of MeSH and 50 000 tonnes/year of DMDS without recycling (comparative - incineration of the stream 11) | 7.3 | 18.3% |
| Unit for co-production of 50 000 tonnes/year of MeSH and 50 000 tonnes/year of DMDS with recycling (invention - recycling of the stream 11) | Negligible | Negligible |

The comparison shows two of the advantages of the process according to the invention. The first advantage is that of avoiding the incineration of sulfur-based products and the release of sulfur oxide into the environment, contributing towards atmospheric pollution. The second is that of improving the yield for the production of MeSH.

The invention claimed is:

1. A process for the co-production of methyl mercaptan and of dimethyl disulfide, comprising the following successive steps:

a) reacting at least one carbon oxide in the presence of hydrogen sulfide ($H_2S$) and hydrogen to form a stream (M) comprising methyl mercaptan, water, and optionally unreacted hydrogen sulfide, b) purifying the stream (M) to obtain a stream (N) enriched in methyl mercaptan and a stream containing uncondensable compounds ($M_{uncond}$), c) optional recycling the stream of uncondensable compounds ($M_{uncond}$) obtained from step b) into step a), d) recovering a first portion of the stream (N) including methyl mercaptan purified in step b), e) oxidizing with sulfur a second portion of the stream (N) of methyl mercaptan, to form a stream (O) comprising dimethyl disulfide, hydrogen sulfide, and optionally unreacted methyl mercaptan, f) purifying the stream (O) to separate the dimethyl disulfide from the hydrogen sulfide and optionally the methyl mercaptan that has not reacted in step e), g) recycling the hydrogen sulfide and possibly the methyl mercaptan isolated in step f) into the stream (M) obtained from step a), h) recovering the dimethyl disulfide isolated in step f).

2. The process according to claim 1, wherein the recycling step g) provides the stream to be recycled before the purification step b), which removes the hydrogen sulfide from the stream (M) to be purified, optionally followed by decantation and/or distillation.

3. The process according to claim 1, wherein the streams containing the hydrogen sulfide, and optionally the methyl mercaptan that has not reacted in step e), is recycled into the stream (M) obtained from step a).

4. The process according to claim 1, wherein in step a), the carbon oxide is carbon monoxide, carbon dioxide or a mixture thereof.

5. The process according to claim 1, wherein in step a), the hydrogen sulfide is generated in situ by adding sulfur and hydrogen.

6. The process according to claim 1, wherein the hydrogen sulfide in step a) is generated from sulfur and a mole ratio of carbon oxide/S/$H_2$S/$H_2$ is between 1/0/0.05/0.05 and 1/20/40/100, or the hydrogen sulfide in step a) is not generated from sulfur and a mole ratio of carbon oxide/$H_2$/$H_2$S is between 1/0.05/0.05 and 1/40/100.

7. The process according to claim 1, wherein the reaction temperature of step a) is between 200° C. and 500° C., the pressure is between 1 and 100 bar absolute, and the reaction of step a) is performed in the presence of a catalyst chosen from molybdenum and potassium catalysts of a Mo—S—K and/or Mo—O—K type on a support.

8. The process according to claim 1, wherein the methyl mercaptan/sulfur mole ratio of the oxidation step e) is between 0.1 and 100.

9. The process according to claim 1, wherein the reaction temperature of the oxidation step e) is between 20° C. and 200° C., the pressure is between 2 and 30 bar absolute, and the reaction of the oxidation step e) is performed in the presence of a basic catalyst chosen from homogeneous, two-phase or heterogeneous catalysts.

10. The process according to claim 1, wherein the purification step b) includes one or more condensations, followed by one or more decantations, and optionally one or more distillations.

11. The process according to claim 1, wherein the purification step f) includes one or more distillation steps, and optionally one or more basic catalysis steps.

* * * * *